(12) United States Patent
Valfiorani et al.

(10) Patent No.: US 10,470,474 B2
(45) Date of Patent: Nov. 12, 2019

(54) GRAIN DRYER

(71) Applicant: INGENIERIA MEGA, S.A., Buenos Aires (AR)

(72) Inventors: Marcelo Norberto Valfiorani, Buenos Aires (AR); Marcelo Eduardo Lombardo, Buenos Aires (AR)

(*) Notice: Subject to any disclaimer, the term of this patent is extended or adjusted under 35 U.S.C. 154(b) by 0 days.

(21) Appl. No.: 16/212,029

(22) Filed: Dec. 6, 2018

(65) Prior Publication Data

US 2019/0174782 A1  Jun. 13, 2019

(30) Foreign Application Priority Data

Dec. 6, 2017 (AR) .............................. 20170103411

(51) Int. Cl.

| | |
|---|---|
| A23B 9/08 | (2006.01) |
| F26B 25/22 | (2006.01) |
| F26B 25/06 | (2006.01) |
| G05D 22/02 | (2006.01) |
| F26B 17/12 | (2006.01) |
| F26B 21/04 | (2006.01) |
| F26B 21/08 | (2006.01) |
| F26B 21/10 | (2006.01) |
| F26B 23/02 | (2006.01) |

(Continued)

(52) U.S. Cl.
CPC .............. *A23B 9/08* (2013.01); *F26B 17/126* (2013.01); *F26B 21/04* (2013.01); *F26B 21/08* (2013.01); *F26B 21/10* (2013.01); *F26B 23/02* (2013.01); *F26B 25/06* (2013.01); *F26B 25/08* (2013.01); *F26B 25/22* (2013.01); *G05D 22/02* (2013.01); *F26B 25/002* (2013.01); *F26B 2200/06* (2013.01); *G01D 21/02* (2013.01); *G01K 1/045* (2013.01); *G01N 27/121* (2013.01)

(58) Field of Classification Search
CPC ........ F26B 17/126; F26B 25/08; F26B 23/02; F26B 21/10; F26B 21/08; F26B 21/04; F26B 25/06; F26B 25/22; F26B 2200/06; F26B 25/002; A23B 9/08; G05D 22/02; G01D 21/02; G01N 27/121; G01K 1/045
See application file for complete search history.

(56) References Cited

U.S. PATENT DOCUMENTS

| | | | | |
|---|---|---|---|---|
| 4,486,960 A | * | 12/1984 | Maurice | F26B 17/122 34/167 |
| 4,714,812 A | * | 12/1987 | Haagensen | F26B 3/343 219/696 |
| 2006/0123655 A1 | * | 6/2006 | Valfiorani | F26B 17/126 34/436 |

* cited by examiner

*Primary Examiner* — Jessica Yuen
(74) *Attorney, Agent, or Firm* — Eugenio J. Torres-Oyola; Victor M. Rodriguez-Reyes; Ferraiuoli LLC (57) ABSTRACT

Grain dryer of the type comprising a vertical main structure consisting of a central body through which the grain to be dried passes, a front hot air intake chamber and a rear used air outlet chamber, being that the main body has in its upper part an entrance from where wet grains are loaded, underneath which there is a loading hopper that communicates with the central body, wherein the grain descends along the central body within which it is dried during its fall by a flow of hot air that passes through the mass of grain, finally exiting through a discharge hopper arranged at the lower end of the dryer, the dryer of the invention being characterized in that it allows to significantly reduce the energy consumption in order to obtain a better quality of grain and a process much faster than conventional ones due to the arrangement of one or more preheating chambers without extraction of moisture from the grain.

7 Claims, 7 Drawing Sheets

(51) Int. Cl.
    *F26B 25/08*     (2006.01)
    *G01K 1/04*     (2006.01)
    *F26B 25/00*     (2006.01)
    *G01D 21/02*     (2006.01)
    *G01N 27/12*     (2006.01)

GRAIN DRYER

FIELD OF THE INVENTION

The present invention relates to the field of agro-industry, and more particularly refers to a grain dryer that, unlike conventional dryers, allows performing the drying process of grains under ideal conditions of humidity and temperature, improving their quality and significantly reducing energy consumption. Even though in the present description reference is made to a grain dryer of the type formed by a column structure from whose upper end the grain volume to be dried is loaded, it should be clear that the invention can be adapted and used in different types and arrangements of grain dryers either independently or jointly with means, devices or related arrangement.

DESCRIPTION OF THE PRIOR ART

A great variety of grain dryers is known in the field of the art, which can be classified according to the structural features that they have for grain displacement path and for the circulation of the drying air thereof. Currently, among the existing dryers, there can be mentioned the column dryers, constituted by a large prismatic body within which vertical walls are defined which are constructed with perforated sheets that divide the columns into which the grain descends, which is loaded through a top inlet, until it leaves the machine through a lower discharge outlet. The perforated walls define channels or columns within which the grain circulates, and between these columns, spaces are defined for the passage of drying air that is previously heated by systems of burners or heaters in general.

In this way, hot air circulates through the spaces provided for this purpose, between grain drying columns and should enter the columns passing through holes of perforated sheets that make up the walls of columns, then it goes through the mass of grain and drags with it moisture contained in it. The grain that is against one of the faces of the corresponding column, tends to continue being "stuck" to that face while it descends, this is the reason why in these dryers there is provided a biasing device on all the column that causes the cereal on one side to move to the other, which is an undoubtedly unfavorable condition during the drying process, since the grain overheats in relation to the other that is next to the opposite face.

To solve these problems, dividing floors are placed that reverse the direction of air circulation, but the grain that is next to the perforated sheet on either side of the column is much hotter than the one in the center of the column. Consequently, the quality of the drying is very poor, causing a very high rate of "cracking" of the grain. In addition, these dryers have floors inside to generate air deviations, which is a serious drawback because it favors the accumulation of "light components" that generate areas with a very high probability of fire sources, which is very frequent in dryers of columns of this type. Likewise, the necessary air backpressure in these dryers is very high, because the air should pass through the perforations of the sheets, so they demand for their operation a large consumption of electrical energy.

Although these machines have been widely used and allow for large spaces for the entry of drying air between the columns that contain grain, in addition to the drawbacks mentioned above, it should be noted that they demand high costs for manufacturing multi-perforated sheets, inside of the columns they form very compact masses where the circulation of the drying air is hindered, and the surface contact of the drying air with the grain is not as efficient as would be expected, and they do not have the desired yield.

Other known and widely used drying machines are known as trestle dryers. These machines have a main body within which there is a plurality of cross section profiles formed by two vertical walls and an angled wall as a saddle roof. This plurality of profiles is arranged transversely across the width of the body of the dryer and defines a staggered or alternating configuration, so as to make the volume of the grain loaded through the upper part of the machine fall on the angled wall formed by the profiles or trestles and open towards the sides thereof to fall on respective angled walls of respective lower trestles which, in turn, generate the same effect on the descending mass of grain. The drying air enters through a front part of the trestles, which have the back part closed and the lower part open, circulating inside them upwards and downwards, passing through the mass of grain, and leaving through a back part of the body of the machine. Unlike column dryers, these trestle dryers generate a good downward flow of grain but do not provide spaces or areas, also called plenums, for the passage of drying air. Consequently, there is also in this case an almost compact mass of grain that hinders its drying.

There are other drying machines called cascade, provided with a plurality of trays in a succession of levels that allow the grain that entered from an upper part of the machine to fall as a cascade on each of the trays, while the drying air is injected and aspirated so that it may pass through the trays and come in contact with the grain. These machines only provide a central area through which the air enters and, after passing through the trays and the grain, it goes out towards the periphery of the machine, so that the use of the thermal capacity of evaporation brought by hot air can not be efficiently used, because it also has to pass through an almost compact mass that descends only by a peripheral sector of the machine. It is important to say that, the mass of grain loaded into the machine is not sectioned into portions of low density to obtain a more uniform contact between the mass of hot air and the mass of wet grain.

In the particular case of conventional grain dryers whose columns include a plurality of deflectors arranged alternately on both side walls. These deflectors have a length such that their ends converge in a vertical central imaginary line that extends along the column. In this way, the flow of grains that descends down the column continuously describes a zigzag path determined by the succession of deflectors that it encounters in its path. It is important to say that, the hot air that enters through each of the inlet openings of the column comes into contact with the grain, passing through the volume thereof as it descends, and leaves the column through the exit openings.

One of the most important deficiencies in this drying process is the "interference" effect that occurs between the deflectors and the volume of grain in the drying process. Consequently, the entire grain volume descends continuously following an alternate zigzag path and is permanently subjected to hot air flows. In other words, the grain is subjected to the circulation of hot air in an enveloping mode over the entire length of the column, practically in the same way as in the column dryers with perforated sheet walls. The resulting grain of this process shows multiple superficial cracks, which is a sign of low quality, precisely, because it has been subjected to a constant heating, without the appropriate times for the progressive and controlled evaporation of the moisture contained therein.

As a result of the above, Argentine Patent Application Serial No. P20040104617, to INGENIERIA MEGA S.A., describes a grain dryer with high thermal performance and stabilized heating of grains during the drying process thereof, this type dryer being composed of a column structure from whose upper end the volume of grain to be dried is loaded and which then follows a downward path essentially in a zigzag way to be subjected to hot air streams that circulate from a succession of air intake, defined in a first side wall of the column, towards a succession of outlets of used air, defined from a second side wall, herein respective deflectors inclined down to guide the drying air stream and determine the path of the grain that descends along the column are arranged inside the column, in correspondence with each of said air inlets and outlets, where between each pair of deflectors corresponding to respective pairs of air inlets and outlets of each column, wall sections are included, at least partially facing each other, which in combination with the extension of said deflectors define zones of grain accumulation and stabilization of the temperature thereof, the deflectors of the first wall extending to an imaginary transversal line coinciding with a longitudinally intermediate zone of the corresponding facing section of the second wall, wherein the ends where each of the deflectors of the first and second walls of the column ends are transversely spaced apart from each other, defining in the column a continuous central longitudinal zone free from interferences for the descent of the grain.

Unlike what has been previously explained in relation to the previous conventional dryers, in this case the volume of grain that descends along the column is passed through by hot air flows spaced apart from each other. It is important to say that, as the volume of grain descends along the column it is subjected to a sequence of hot air flows that circulate exclusively between one of the inlets and one of the outlets of air, thus forming hot air streams between which zones of temperature stabilization are defined where a part of the volume of grain does not receive direct drying air, its temperature remains practically constant, the elimination of moisture contained is more gradual until the grain is subjected to another stream of drying air in accordance with the next pair of inlets and outlets that it encounters immediately below during its descent and so on.

As a result of this process of progressive heating with zones of temperature stabilization, the grain reaches a final drying with an appropriate residual humidity index and a cracking which is considerably much lower than that of the grains dried by means of conventional dryers, which is an unquestionable evidence of the high quality of the grain thus processed. This is possible due to the special location and extension of deflectors and the dimensional relationship of the parts operatively linked to them, so that side walls of each column have straight sections that together define a succession of temperature stabilization zones or "tempering" of the volume of grain that accumulates during its passage on the deflectors.

It is important to say that, as the volume of grain descends along each column, several special features are observed that are combined during the drying process: the zigzag path of the volume of grain is less abrupt than in conventional dryers; the length of the deflectors determine inside the columns a central longitudinal zone free of interference for the grain descent; the straight sections defined in each wall of the columns between each air inlet and each air outlet allow the accumulation of a certain amount of grains in the corresponding "tempering" zones; and the circulation of hot air occurs exclusively between each of the inlets and the respective air outlet located lower than the corresponding inlet.

Consequently, grain drying takes place through successive stages of heating and temperature stabilization, or "tempering", where the grain loses the moisture contained in a regulated and homogeneous way. The result, as already expressed, is a grain of optimum quality in terms of the final residual moisture required and a considerably low rate of cracking thereof.

Although the conventional dryers of the prior art have proved to work correctly in practice, there are still a number of drawbacks among which we can observe the high energy consumption involved in the dryers that exist today and that could not be solved so far. Thus, by virtue of the foregoing, it would be convenient to have a new arrangement, device or dryer that dramatically reduces energy consumption without affecting the quality of the grain, and allows optimizing operating times of the drying process.

BRIEF DESCRIPTION OF THE INVENTION

It is therefore an object of the present invention to provide a new grain dryer that makes it possible to significantly reduce energy consumption in order to provide a much faster process and a better grain quality.

It is also another object of the present invention to provide a grain dryer that has a grain preheating chamber that without removing moisture, allows a better drying process thereof.

It is still another object of the present invention to provide a grain dryer that has a programmable logic controller that depending on the moisture conditions of the grain will allow performing the drying according to the object of the present invention or, in accordance with conventional processes.

It is another object of the present invention to provide a grain dryer of the type comprising a vertical main structure composed of a central body through which the grain to be dried passes, a front hot air intake chamber and a rear used air outlet chamber, being that the main body has in its upper part an inlet from where wet grains are loaded, below which there is a loading hopper that communicates with the central body, wherein the grain descends along the central body inside which it is dried during its fall by a flow of hot air that passes through the mass of grain, and finally exits through a discharge hopper arranged at the lower end of the dryer, wherein said central body comprises a plurality of contiguous modules; said front hot air intake chamber is provided with at least one vertical partition and at least one horizontal partition arranged adjacent between two contiguous modules, the vertical partition and the horizontal partition together defining at least two completely isolated sectors; said rear used air outlet chamber is provided with at least one vertical partition that extends from the upper part of the dryer downwards, being in linear alignment with the horizontal partition of the front chamber, said vertical partition being provided with at least one pivoting gate that operates between opening and closing positions, and being in turn that, at least one fan is provided which is arranged transversely to the vertical partition and adjacent between contiguous modules; thus defining, between one of the two isolated sectors defined by the vertical-horizontal partitions of the front chamber, the vertical partition—fan—pivoting gate in the closed position of the front chamber and at least two contiguous modules of the central body of the dryer, at least one grain preheating chamber.

BRIEF DESCRIPTION OF DRAWINGS

For greater clarity and understanding of the object of the present invention, it has been illustrated in several figures, in which the invention has been represented in one of the preferred embodiments, all by way of example, wherein.

DETAILED DESCRIPTION OF THE INVENTION

Referring now to the figures, it is seen that the invention consists in a new grain dryer that allows carrying out the drying process under ideal conditions of temperature-humidity, thus obtaining a better grain quality, and achieving a significant reduction in the energy consumption.

First and for merely exemplary purposes to provide a better understanding of the object of the present invention, reference will be made to the grain dryer of the Argentine Patent Application No. P20040104617 of INGENIERIA MEGA S.A. According to FIGS. 1 to 4 related to the prior art, it can be seen that INGENIERIA MEGA S.A.'s dryer comprises a vertical main structure 1, composed of a central body 2, through which the grain to be dried passes, a front chamber 3 for entering hot air and a rear chamber 4 for the exit of the air used. The main body 2 has in its upper part an inlet 5 from which wet grains are loaded, below which there is a loading hopper 6 that communicates with the central body 2.

Figure 1:
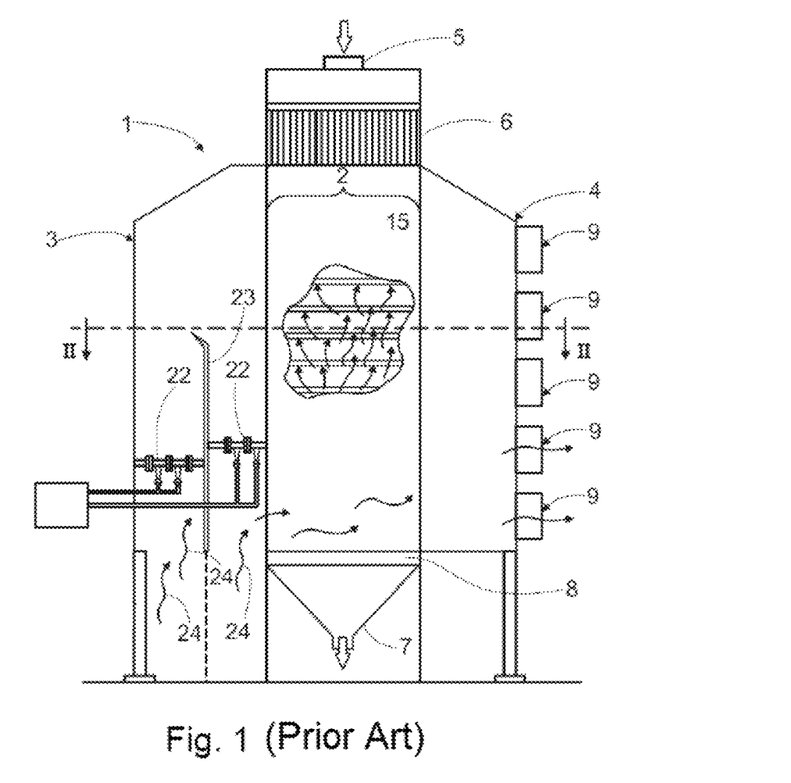
FIG. 1 shows a front and partial sectional view of a grain dryer according to the prior art.

The wet grain enters through the upper inlet 5 and descends along the central body 2 inside which it is dried during its fall by the hot air that passes through the grain mass, and finally it exits through a discharge hopper 7 arranged at the end bottom of the dryer, after controlling its exit and distribution by means of a discharge table 8. The air enters the chamber 3 and is heated by means of burners 22 which can be operated by various types of fuels and located in different positions. Inside the chamber 3 one or more partitions 23 can be arranged so as to direct the air in the desired manner, according to the latter, it enters as indicated by the arrows 24 from the bottom of the structure of the drying machine. The drying machine is mounted by means of appropriate columns to leave its lower part open, thus facilitating the entry of air and its free circulation.

Figure 2:
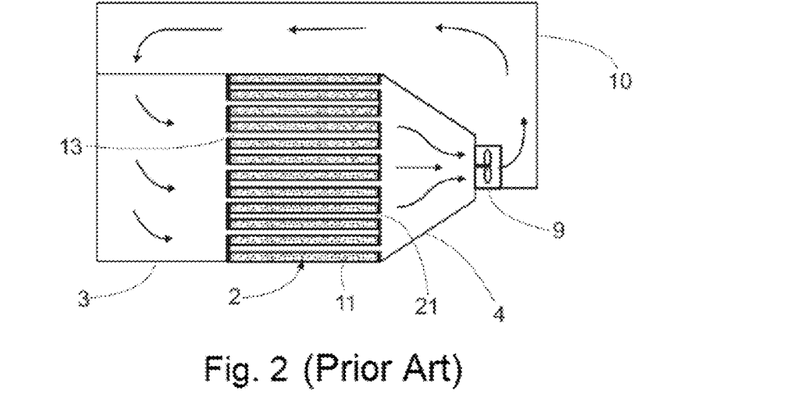
FIG. 2 shows a view of the section II-II made in FIG. 1 related to the prior art.

FIG. 2 of the prior art and corresponding to the cross section according to lines II-II drawn in FIG. 1, clearly shows the main sectors of the grain drying machine as they have been identified in FIG. 1, showing the central body 2, the hot air inlet chamber 3, the used air outlet chamber 4, the assemblies for air suction fans 9 and, optionally, the recirculation line 10 for used air carrying the air exiting through the fans 9 again to the drying air inlet chamber 3 in order to take advantage of the available thermal energy.

Figure 3:
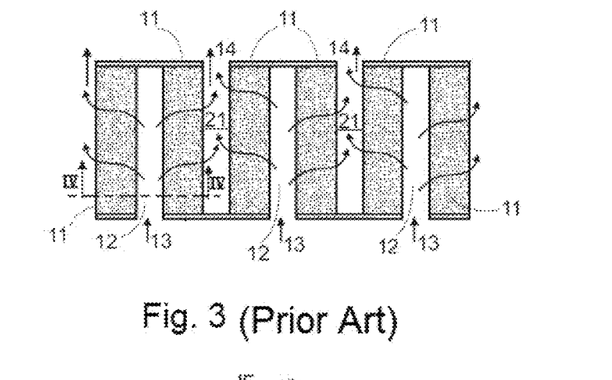
FIG. 3 shows a partial sectional view of a part of the grain dryer of FIG. 1.
Figure 4:
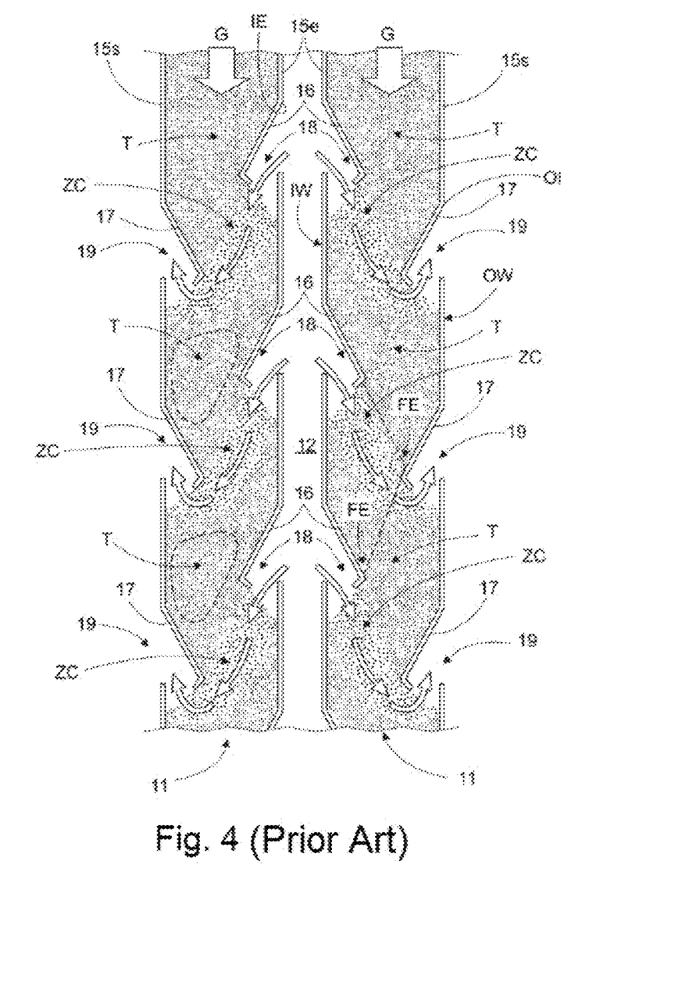
FIG. 4 shows a sectional view of a part of the conventional dryer of FIG. 1 and according to the prior art.

In FIGS. 3 and 4 related to the previous art, it can be seen that the central body 2 is composed of vertical columns 11, along which the wet grain loaded in the upper hopper 5 descends towards the lower hopper 7 from where the grain already dried comes out. Between columns 11, spaces or areas 12 are arranged for the circulation of hot air that enters through the air inlets 13 and it exits through the used air outlets 14, as indicated by the arrows drawn in FIG. 3 of the previous art.

In FIG. 4 of the prior art, corresponding to the cut IV-IV indicated in FIG. 3, it is shown that each of the columns 11 is composed of lateral walls 15e and 15s, each of which has opposite deflectors 16 and 17 alternately arranged, which are respectively associated with hot air inlet openings 18, on one of the side walls 15, and used air outlets 19, defined on the side walls opposite to the former ones, on each of the columns 11.

While the grain descends, the hot air entering through the inlets 13, defined between adjacent columns 11, circulates through the areas 12 and then passes through the air inlet openings 18, passes through the mass of the grain that is inside the columns 11 and finally exits through the openings 19. Next, the air leaving the columns 11 reaches the outlet areas 21 which are alternately arranged between the air inlet areas 12 and between the corresponding columns 11.

The air that enters from the bottom to the chamber 3 and passes through the burners 22 (see FIG. 1) gives the mass of grain the heat necessary to evaporate the moisture it contains while circulating through the columns 11. The air inlet openings 13 shown in FIG. 3 (Prior Art) are oriented towards the air intake chamber 3, so that the air once heated by the burners 22 enters the openings 13, passes through the spaces 12, the openings 18 of the columns 11, passes through the mass of grain that descends inside the columns 11, then it exits through the openings 19 as indicated by the corresponding arrows drawn in FIG. 4, passes through the outlet passages or spaces 21 (see FIG. 3) and finally flows into the used air chamber 4 by the suction generated by the fans 9.

FIG. 4 of the prior art allows to clearly appreciate that between contiguous hot air inlets 18 and between contiguous used air outlets 19 of each column 11 respective sections of the walls 15e and 15s are included, at least partially facing each other, which in combination with the extension of the deflectors define areas of grain accumulation and temperature stabilization thereof, or "tempering" zones, hereinafter indicated with the reference T. The deflectors 16 of the wall 15e and the deflectors 17 of the wall 15s extend downwards to an imaginary transversal line coinciding with a longitudinally-medial area of the corresponding opposite section of the opposite wall. The ends where each of the deflectors 16 and 17 ends are spaced from each other, defining in the columns 11 a continuous central longitudinal zone free of interference for the descent of the grain.

The "tempering" zones T are essentially defined above each of the deflectors 16 and the sections of the opposite wall 15s, as well as above the deflectors 17. In addition, between an upper part of each of the upper sections of the walls 15e and 15s, respectively adjacent to the inlet 18 and outlet 19 openings of the air, there is defined a zone ZC of hot air circulation for direct drying of the grain, with downward path from each air inlet opening 18 to the respective air outlet opening 19 which is located longitudinally lower in the columns 11.

This conventional structural configuration of the grain dryer allows that during the drying process the volume of grain, which descends along each column 11, is passed through by hot air flows spaced apart from each other, as indicated in zones ZC, the grain thus being subjected to a sequence of hot air flows that circulate exclusively between pairs of air inlet and outlet openings 18 and 19, forming hot air streams between which the temperature stabilization or "tempering" zones T are defined. In this way, in the T zones the grain does not receive direct hot air flow, thus making it possible to maintain the temperature of the grain practically constant, causing the elimination of the humidity contained more gradually during the drying process and, consequently, a lower cracking of the grain, which, as already expressed, is an indicator that shows the quality of the dry grain obtained.

Although, the grain dryer of the Argentine Patent Application Record No. P20040104617 of INGENIERIA MEGA S.A. has proven to work correctly in the practice, the high energy consumption is a factor that has not yet been solved in any of the existing conventional grain dryers. As a result of the above, the present invention is aimed at providing a grain dryer that notably solves the drawback of energy consumption apart from providing a better grain quality. It is clarified that, same reference numerals shall be used to describe those equal parts between the prior art dryer and the dryer of the invention, while reference numbers from 100 shall be used to describe those new parts according to the present invention.

Thus, and according to FIGS. 5 to 8, the grain dryer of the present invention is indicated by the general reference 101 and comprises in general, a vertical main structure composed of a central body 2 through which the grain to be dried passes, a front chamber 3 for the entry of hot air and a rear chamber 4 for the exit of the air served. The main body 2 has in its upper part an inlet 5 from which wet grains are loaded, below which there is a loading hopper 6 that communicates with the central body 2.

Figure 5:
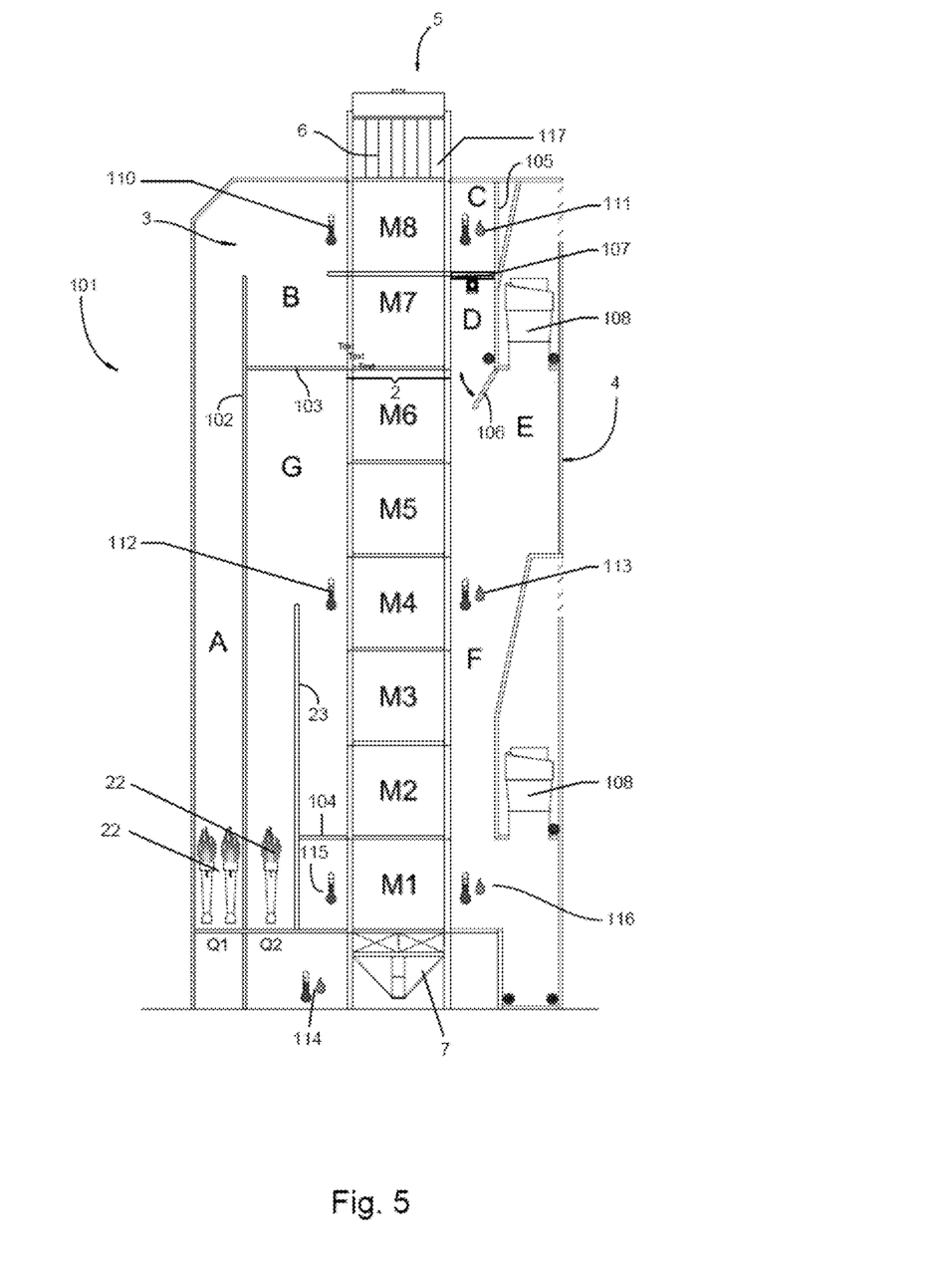
FIG. 5 shows a sectional view of a grain dryer according to the present invention.

It should be noted that the central body 2 of the invention is divided into several modules "M" and that, for merely exemplary purposes to simplify the understanding of the present invention, it has been decided to list them in ascending order as M1, M2, M3, M4, M5, M6, M7 and M8, this being not limiting for the present invention, but different amounts of modules can be used without any inconvenience.

As mentioned above, the wet grain enters through the upper inlet 5 and descends along the central body 2 inside which it is dried during its fall by the hot air that passes through the grain mass, and finally exits through a discharge hopper 7 arranged at the lower end of the dryer. The air enters the chamber 3 and is heated by means of burners 22 which can be operated by various types of fuels and located in different positions. Inside the chamber 3, one or more partitions 23 can be arranged so as to direct the air in the desired manner, as the latter enters.

One of the novel features of the present invention is that the chamber 3 has a second vertical partition 102 which extends beyond the height of the partition 23, remaining in linear adjacency with the corresponding part between modules M7 and M8, as best illustrated in FIG. 5. Likewise, there is a horizontal partition 103 which is arranged transversely to the vertical partition 102 between module M6 and M7. The arrangement of vertical partitions 102 and horizontal partitions 103 makes it possible to define, within chamber 3, at least two completely isolated sectors, which are composed of at least one sector A is in communication with a sector B and at least one sector G completely separate from these two sectors.

In this way, the air entering through the lower part of the grain dryer passes through the burners 22 arranged in a sector Q1 and moves from sector A to sector B, which is only in communication, but not limited for the invention, with modules M7 and M8 through which the grain to be dried constantly descends. Simultaneously, the other part of the air entering through the lower part of the dryer passes through another set of burners 22 of a sector Q2, and moves to sector G which is in communication with modules M2, M3, M4, M5 and M6.

Sector G has a lower horizontal partition 104 between module M1 and M2, in such a way that module M1 is isolated from the rest and functions as a module or chamber for cooling the grain inside the dryer since it does not have any burner, this partition 104 has the possibility of being placed at different heights of module M1 to regulate the cooling, also avoiding this cooling by drying at full heat. That is, in module M1, the grains are cooled (if the process needs it), previously to fall in the discharge hopper 7, while between modules M6 to M2 the traditional drying of the grain is carried out as it has been described above and that for such reasons, we will not go into more descriptive details about its operation.

On the other hand, the chamber 4 has a vertical partition 105 that extends from the upper part of the dryer downwards, being in linear adjacency with the corresponding part between module M6 and M7 and in turn, in linearity with the horizontal partition 103 of the front chamber 3. Wherein, said partition 105 is provided at its lower end with at least one pivoting gate 106 that operatively insulates the air flow corresponding to modules M7 and M8 from the rest. Likewise, chamber 4 has a fan 107 between modules M7 and M8, thus defining an upper sector C adjacent to module M8 and a lower sector D adjacent to module M7.

Figure 6:
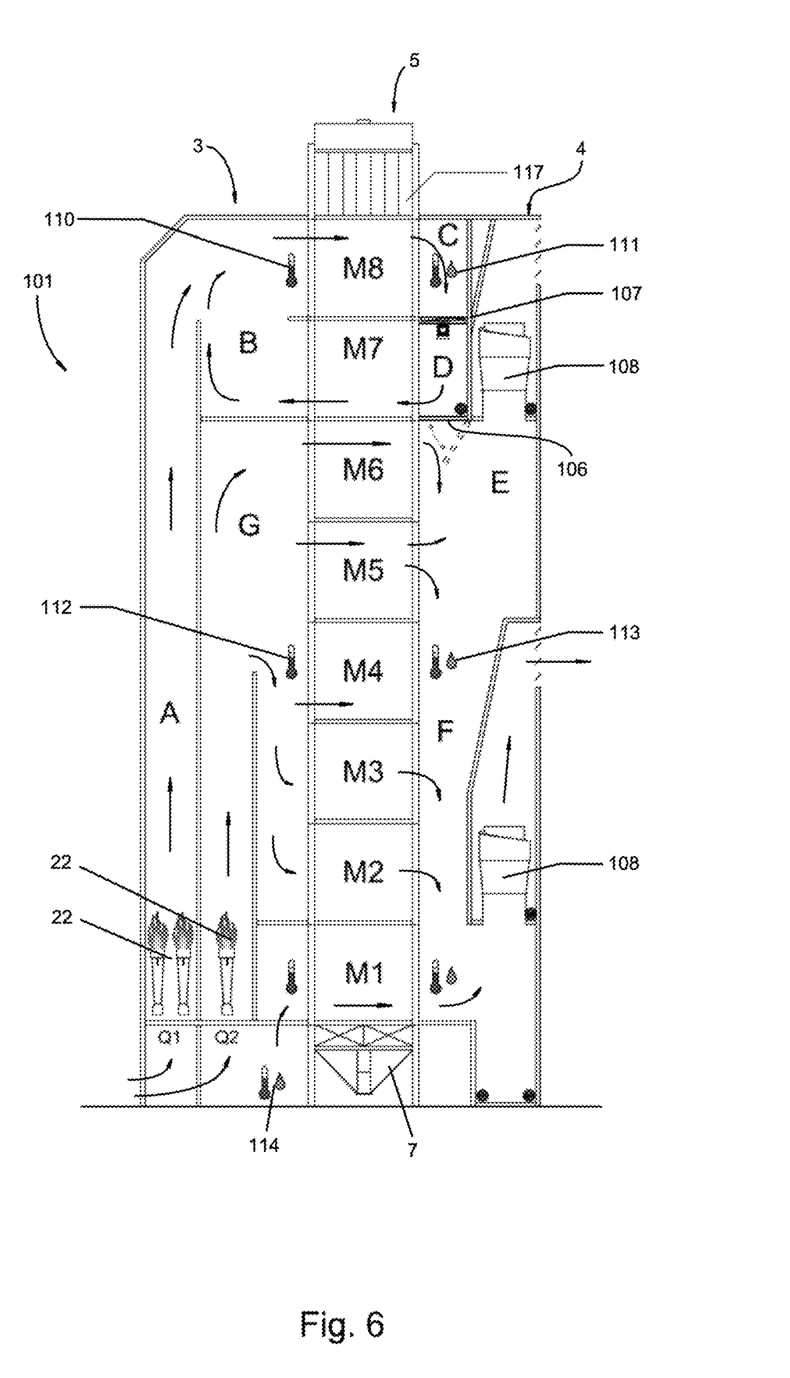
FIG. 6 shows a sectional view of the grain dryer of FIG. 5, wherein it is illustrated in operation mode according to the present invention.
Figure 7:
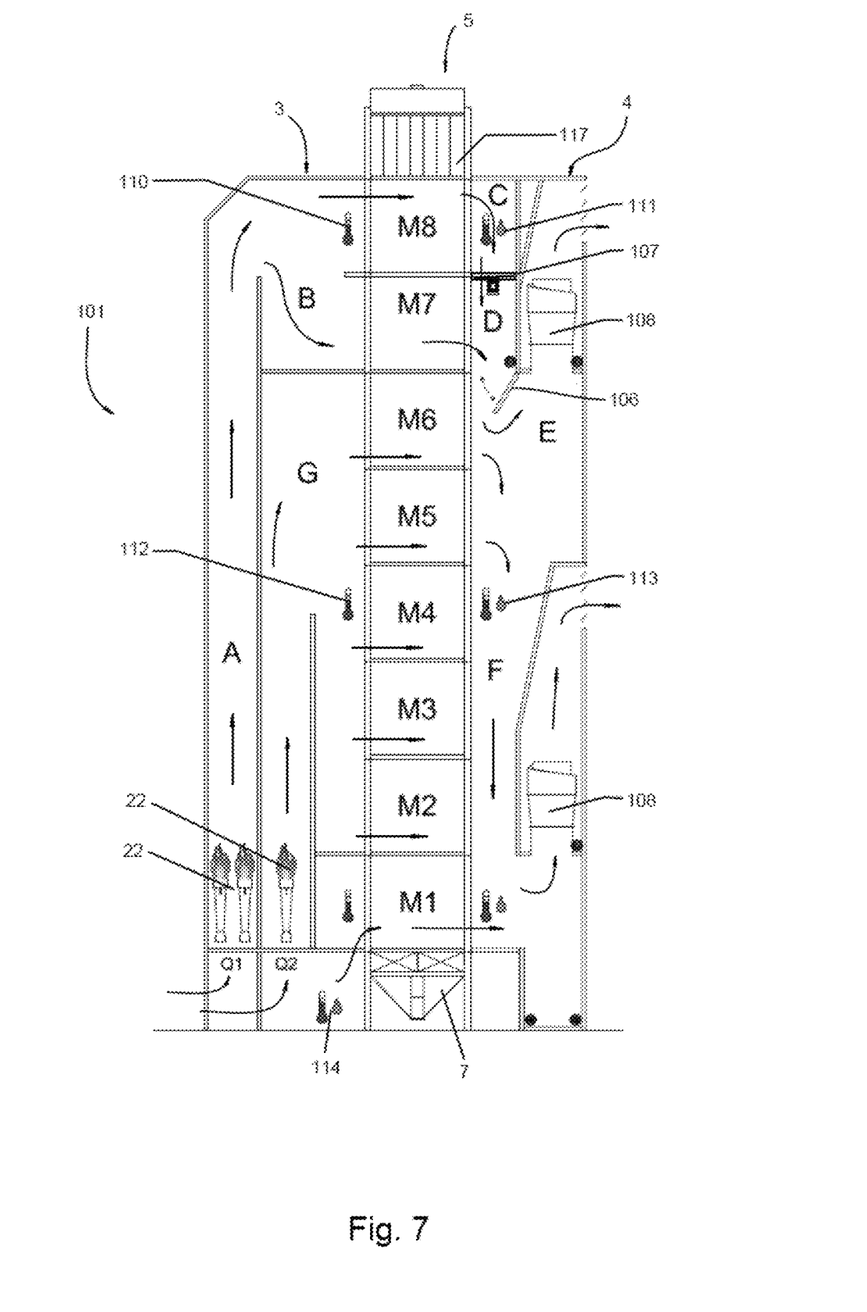
FIG. 7 shows a sectional view of the grain dryer of FIG. 5, where it is illustrated in another mode of operation according to the present invention.

In this way, when the gate 106 is closed, there is defined a pre-heating chamber C-D-B for pre-heating the wet grain which passes through the M7 and M8 modules in order to be pre-heated without moisture extraction, and then it continues descending and continuing with the usual drying process thereof until arriving at the discharge hopper 7, as mentioned above. Sector D is in communication with a sector F arranged adjacent to modules M1 to M6 and which, in turn, is in communication with at least one pair of air extraction fans 108.

Figure 8:
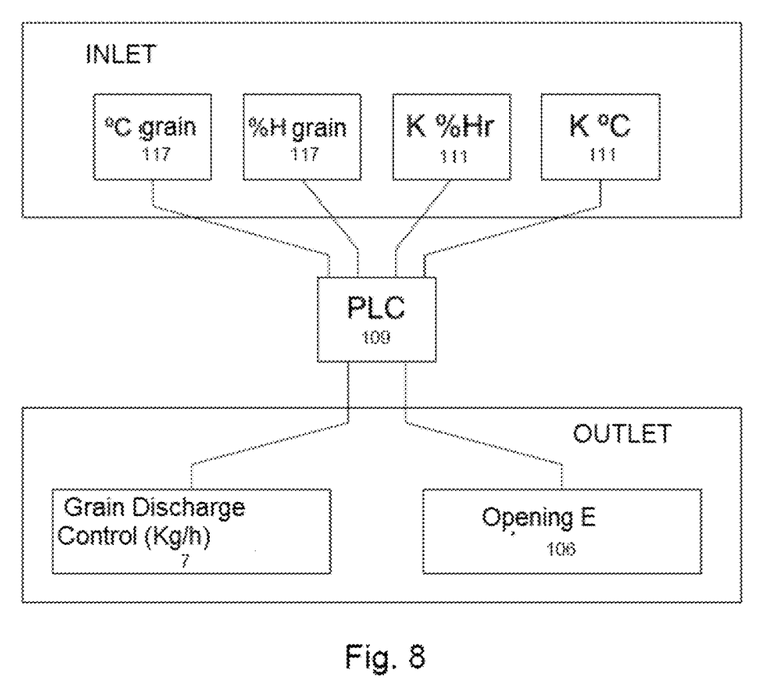
FIG. 8 shows a block diagram of the programmable logic controller according to the present invention.

On the other hand, in order to carry out the opening or closing of the gate 106, it is connected to a motor (not shown) which in turn is operated by means of a programmable logic controller (PLC) 109. The PLC 109 is connected to a plurality of temperature and humidity sensors between which, at least a temperature sensor 110 in sector B and at least one set of temperature-relative humidity sensor 111 in sector C can be provided. Likewise, the dryer of the present invention has at least a temperature sensor 112 in sector G, at least one set of temperature-relative humidity sensor 113 in sector F, at least one set of temperature-relative humidity sensor 114 in the lower part of the dryer through which the air enters module M1, at least a temperature sensor 115 at the inlet of module M1, and at least one set of temperature-relative humidity sensor 116 at the output of module M1.

Thus, ambient air enters chamber A passing through burner Q1, takes heat energy from it and passes through the (full) grain carrying columns of module M8, delivering the caloric energy obtained in Q1 to the grain. At the outlet of sector C, temperature and humidity values of the air are measured by means of the temperature-relative humidity sensor set 111 strategically placed therein and it passes to sector D driven by fan 107, causing flow to module M7 also full of grain. This is caused by the pressures and drops generated by the fan 107, thus an air circulation occurs with temperature and saturated humidity that does not allow the removal of moisture from the grain and causes its heating, that is, hot air re-circulates making the circuit: sector B-C-D through modules M8 and M7 heating the grain without moisture extraction, prior to its usual drying process.

It is emphasized that modules M8 and M7 are divided into their air channels, for which reason the air is forced to pass through the aforementioned circuit. That is, since modules M7 and M8 are "separated" from the rest, hot air enters through sector B, passes through module M8—sector C—fan 107—sector D—and returns through module M7 to sector B again, and so on while the gate 106 is closed. In turn, said sectors C and D communicate with sector F by means of gate 106. In the case where sensors 117 placed in the receiving hopper 6 register a very high humidity, the gate would open and let pass moisture-laden air to produce drying in the traditional way.

Simultaneously to the previous process, ambient air enters sector G passing through burner Q2, takes energy from it, then it passes through the columns (full of grains) of modules M6, M5, M4, M3 and M2 producing the drying in the traditional way, at the outlet of modules, it enters sector F where the temperature and relative humidity of the outlet air are measured by means of the temperature-humidity sensor set 113 and then goes outside by means of fans 108 that perform their function. In module M1, like traditional machines, the air enters through a chamber that does not have burners and has the function of cooling the grain. In this way, the grain is preheated between modules M8 and M7, without extraction of moisture, and then follows its usual drying process according to the prior art techniques mentioned above.

Figure 9:
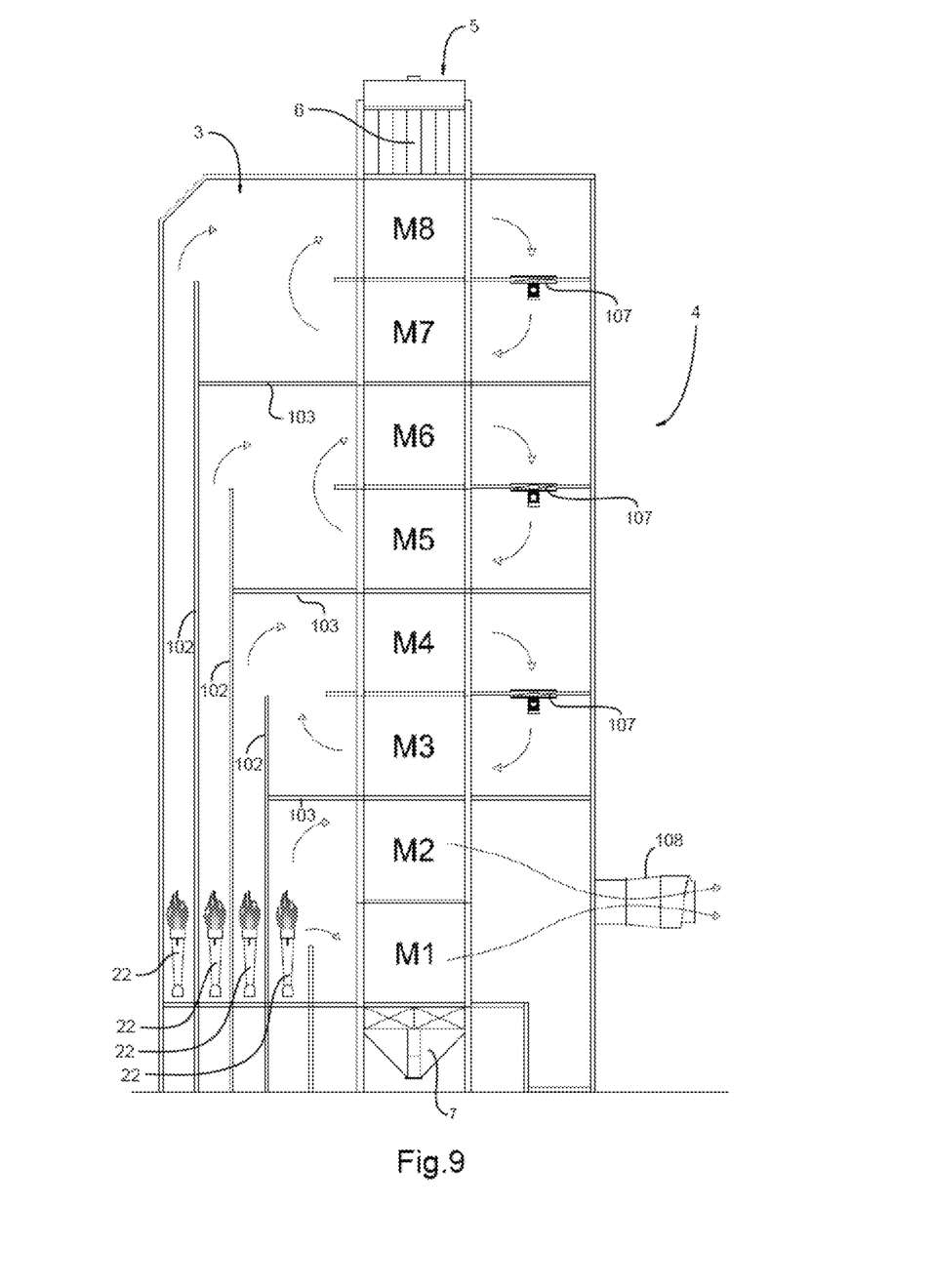
FIG. 9 shows a sectional view of an alternative preferred embodiment of the dryer of the present invention.

According to FIG. 9, in a second preferred embodiment, but not being limiting for the invention, the structural configuration defined above of the recirculation and heating modules 7 and 8 (without the gate 106) can be extended to other pairs of modules such as for example modules M5 and M6, M4 and M3, or M2 and M1, where only the grain will be heated as it happens in some oil extraction processes in which it is dehusked and hot cracked without the need to dry. In this way, it is demonstrated that the object of the present invention can be adapted and used without any inconvenience for various products.

By way of example, but not limiting the present invention, the pivoting gate 106 remains closed provided that desired or maximum values are recorded, wherein said values that sensors can measure as maximum parameters are the following: temperature sensor 110: maximum admissible temperature 100° C.-110; temperature-relative humidity sensor set 111: maximum admissible values: outlet temperature 45° C.-55% relative humidity. In the event that values above the desired values are recorded, or the humidity percentage detected by the sensor 117 is greater than the maximum value, for example, 20-22% (process-dependent value), the PLC 109 emits a signal to carry out the opening of the gate 106, the drying process is carried out in the conventional manner, as better illustrated in FIG. 7. The PLC has a built-in algorithm which makes decisions on the gate 106 and on the control of the discharge (tilting 7) depending on the measured values of temperature-humidity in the different points indicated. On the other hand, by conventional dryers of the prior art, a usual process of grain drying involves an energy consumption which shall vary with the different grain species and humidity range, but to give an example with values obtained in a test equipment, in the soybean variety with an initial 12% moisture content to reduce to 9% moisture content (prior to the oil production process), 2530 Kcal/kg of evaporated water was used in the traditional manner, which was reduced to 1560 kcal/kg of evaporated water, with the new system being this a significant advantage over the previous art.

By means of the invention, it is demonstrated that not only a significant reduction in energy consumption is obtained, but also a better final grain quality is obtained with a very low residual relative humidity and a much faster drying process. In this way, the grain dryer of the present invention is constituted and constructed.

The invention claimed is:

1. A grain dryer comprising:
   a vertical main structure comprising
      a central body through which the grain to be dried passes;
      a front hot air intake chamber;
      a rear used air outlet chamber;
      an inlet from where wet grains are loaded;
      a central body located under said inlet;
      a discharge hopper arranged at the lower end of the said main structure;
   wherein
      said central body comprises a plurality of contiguous modules;
      said front hot air intake chamber comprises at least one vertical partition and at least one horizontal partition arranged adjacent between two contiguous modules, the vertical partition and the horizontal partition together defining at least two completely isolated sectors;
      said rear used air outlet chamber comprises at least one vertical partition that extends from the upper part of the dryer downwards, being in linear alignment with the horizontal partition of the front chamber, said vertical partition being provided with at least one pivoting gate that operates between opening and closing positions, and being in turn that, at least one fan is provided which is arranged transversely to the vertical partition and adjacent between contiguous modules, and
      at least one grain preheating chamber is defined between one of the two isolated sectors defined by the vertical-horizontal partitions of the front chamber, the vertical partition, the fan, the pivoting gate in the closed position of the front chamber and at least two contiguous modules of the central body of the grain dryer.

2. A grain dryer according to claim 1, wherein one of the totally isolated sectors of the front chamber comprises a first sector in communication with a second sector, said first sector having in its lower part a set of burners, while second sector is in communication with at least two contiguous modules and comprises at least a temperature sensor.

3. A grain dryer according to claim 2, wherein the other sector of the totally isolated sectors comprises a third sector provided with at least one vertical partition and a set of burners, wherein the third sector is in communication with the remaining modules of the main body and has at least a temperature sensor.

4. A grain dryer according to claim 3, wherein said vertical partition-pivoting gate and fan define at least one fourth sector and one fifth sector, the fourth sector comprising at least a temperature-relative humidity sensor set.

5. A grain dryer according to claim 4, further comprising a grain cooling module comprised of a lower module of the main structure, between the discharge hopper and the modules corresponding to the third sector of the front chamber, which is adjacent to a temperature-relative humidity sensor set.

6. A grain dryer according to claim 4, wherein the rear chamber comprises a sixth sector in communication with the fifth sector of the rear chamber, wherein said sixth sector is provided with respective air exhaust fans and at least one temperature-relative humidity sensor set arranged adjacent to the corresponding lower module with the cooling chamber.

7. A grain dryer according to claim 4, further comprising a programmable logic controller that is connected to at least said pivoting gate, said temperature sensors, and said temperature-relative humidity sensor set.

* * * * *